(12) United States Patent
Salazar

(10) Patent No.: US 8,592,391 B2
(45) Date of Patent: *Nov. 26, 2013

(54) METHOD FOR THERAPEUTIC, CLINICAL AND VETERINARY USE POLY-ICLC

(76) Inventor: Andres Salazar, Washington, DC (US)

( * ) Notice: Subject to any disclaimer, the term of this patent is extended or adjusted under 35 U.S.C. 154(b) by 151 days.

This patent is subject to a terminal disclaimer.

(21) Appl. No.: 12/285,963

(22) Filed: Oct. 17, 2008

(65) Prior Publication Data

US 2009/0087454 A1 Apr. 2, 2009

Related U.S. Application Data

(63) Continuation-in-part of application No. 10/611,614, filed on Jul. 1, 2003, now Pat. No. 7,439,349.

(51) Int. Cl.
*C07H 19/04* (2006.01)
*A01N 43/04* (2006.01)
*A61K 31/70* (2006.01)

(52) U.S. Cl.
USPC .......................................... 514/48; 536/26.1

(58) Field of Classification Search
None
See application file for complete search history.

(56) References Cited

PUBLICATIONS

Salazar et al. Neurosurgery, vol. 38, No. 6, Jun. 1996.*
Levy et al. Applied Bioactive Polymeric Materials, 1988.*
Wong et al. Antimicrobial Agents and Chemotherapy, Nov. 1995, p. 2574-2576.*
Bektemirov et al. Vopr Virusol. Jan. 1980;(1) 76-8, abstract only.*
The Centers for Disease Control and Prevention, Genomics/Genetic Testing, internet article, May 17, 2011.*
Press, "Genetic Testing and Screening," in From Birth to Death and Bench to Clinic: The Hastings Center Bioethics Briefing Book for Journalists, Policymakers, and Campaigns, ed. March Crowley (Garrison, NY: The Hastings Center, 2008), 73-78.*
Hubbard, The New England Journal of Medicine 1996;334:1192-1194, May 2, 1996.+.*

* cited by examiner

*Primary Examiner* — Layla Bland
(74) *Attorney, Agent, or Firm* — Max Stul Oppenheimer

(57) ABSTRACT

We disclose here a method for using Poly-ICLC to prevent and/or treat certain human and veterinary infectious, neoplastic and autoimmune disorders, as well as for regulating a broad variety of genes in humans, consisting of use of poly-ICLC repeatedly and at low doses, alone or in combination with other drugs or vaccines. As such it represents an example of broad spectrum host-targeted therapeutics, in contrast to conventional antibiotics, antiviral or antineoplastic agents that target specific organisms or tumors.

4 Claims, 5 Drawing Sheets

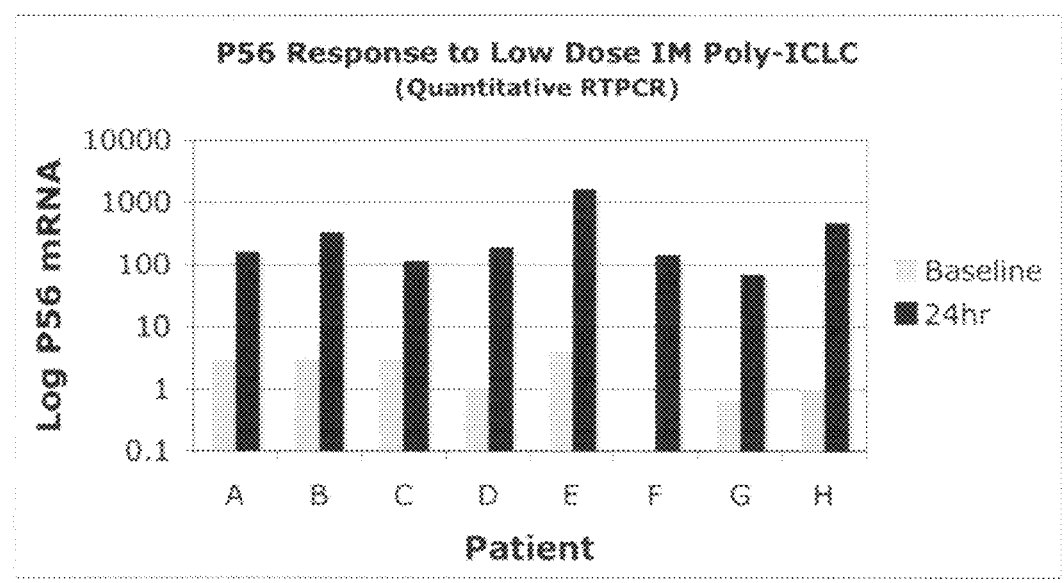
Figure 1. P56 Gene Response to Intramuscular Poly-ICLC in Humans

Figure 2: Percent Survival of Malignant Glioma Patients treated with Poly-ICLC 20 mcg/kg IM two to three times weekly for 1 to 5 years.

| Survival | GBM<br>12 patients | AA<br>11 patients | AA (pf)<br>11 patients |
|---|---|---|---|
| 1 yr | 92% (50%†) | 100% | 100% |
| 2 yr | 50% | 100% (50%†) | 91% |
| 3 yr | 25% (2.2%†) | 91% | 82% |
| 4 yr | 17% | 91% | 82% |
| 5 yr | 8% | 91% | 73% |
| 8 yr | 8% | 82% | 36% |

GBM = glioblastoma, AA = anaplastic astrocytoma, pf = progression free survival, † = Expected survival on standard treatment with radiation and chemotherapy.

Figure 3:

Protection from Lethal SARS Coronavirus Challenge by Nasal Poly-ICLC in Mice

| Group and Dose | Dosing regimen (Hrs pre-post Viral Challenge | #survivors /total | % survival |
|---|---|---|---|
| Placebo control | -24 +24 +48 | 0/10 | 0% |
| Poly-ICLC (5 mg/kg/d) | -24 +24 +48 | 10/10 | 100% |
| Poly-ICLC (1 mg/kg/d) | -24 | 10/10 | 100% |
| Poly-ICLC (0.5 mg/kg/d) | -24 +24 +48 | 10/10 | 100% |
| Poly-ICLC (0.25 mg/kg/d) | -24 +24 +48 | 10/10 | 100% |

Figure 4. Poly-ICLC Treatment of AIDS, Viral Load

Group I: Poly-ICLC Plus Zidovudine

| PATIENT Number | P-24 Antigenemia (pcg/ml) | | | | | | |
|---|---|---|---|---|---|---|---|
| | Months Base | 4 | 8 | 12 | 16 | 20 | 24 |
| PR-O1 | 89 | 15 | 21 | 305 | D | D | D |
| PR-O2 | 45 | 20 | 140 | - | D | D | D |
| PR-O3 | 0 | 80 | 34 | - | D | D | D |
| PR-O4 | 0 | - | 78 | 0 | 0 | 0 | 0 |
| PR-05 | 0 | - | - | - | - | - | - |
| PR-06 | 200 | - | 310 | D | D | D | D |
| PR-O7 | - | 346 | 35 | - | D | D | D |
| PR-O8 | - | 78 | 42 | 0 | 0 | 0 | 0 |
| 04-056 | 12 | 0 | 57 | - | D | D | D |
| PR-10 | 72 | - | - | 0 | 0 | 0 | - |
| PR-11 | 80 | 37 | - | 0 | 0 | 0 | - |
| PR-12 | 76 | 37 | - | 0 | 0 | 0 | - |
| PR-13 | 85 | - | 16 | 11 | 0 | D | D |
| PR-16 | 0 | 0 | 0 | 0 | - | - | - |
| PR-24 | 0 | 0 | 0 | 0 | - | - | - |

Group II: Poly-ICLC Alone

| PATIENT Number | P-24 Antigenemia (pcg/ml) | | | | |
|---|---|---|---|---|---|
| | Base | 4 | 8 | 12 | 16 |
| PR-15 | 0 | 0 | 0 | D | D |
| PR-17 | 0 | 0 | 0 | 0 | - |
| PR-18 | 0 | - | 0 | 0 | - |
| PR-19 | 117 | 31 | D | D | D |
| PR-20 | 0 | 0 | 0 | 0 | - |
| PR-21 | 0 | 0 | 0 | 0 | - |
| PR-22 | 0 | 0 | 0 | 0 | - |
| PR-23 | 808 | 704 | 440 | 200 | - |

(-) = Not done, (D) = Died

710    Figure 5. Poly-ICLC Treatment of Progressive Multiple Sclerosis

CHRONIC-PROGRESSIVE MS

| SEX/AGE | Mos. On PICLC | EDSS-E | AI-E | EDSS-L | AI-L | EDSS Change | Change Per yr. |
|---|---|---|---|---|---|---|---|
| F/29 | 128 | 7 | 8 | 8.5 | 9 | 1.5 | 0.1 |
| F/35 | 82 | 8.5 | 9 | 10 | 9 | 1.5 | 0.2 |
| M/25 | 27 | 7 | 8 | 10 | 9 | 3 | 1.3 |
| M/42 | 189 | 5 | 5 | 7.5 | 6 | 2.5 | 0.2 |
| F/39 | 136 | 8 | 9 | 9 | 9 | 1 | 0.1 |
| M/28 | 12 | 6 | 5 | 5.5 | 3 | -0.5 | -0.5 |
| M/22 | 45 | 7.5 | 7 | 8.5 | 9 | 1 | 0.3 |
| F/61 | 121 | 6.5 | 5 | 8 | 5 | 1.5 | 0.1 |
| M/49 | 164 | 6 | 4 | 6.5 | 6 | 0.5 | 0.0 |
| F/39 | 114 | 8 | 8 | 8 | 8 | 0 | 0.0 |
| M/46 | 13 | 9 | 9 | 7 | 7 | -2 | -1.8 |
| M/25 | 42 | 7 | 6 | 7.5 | 8 | 0.5 | 0.1 |
| F/59 | 26 | 5.5 | 4 | 6 | 3 | 0.5 | 0.2 |
| M/41 | 25 | 8.5 | 9 | 8.5 | 9 | 0 | 0.0 |
| F/62 | 6 | 7.5 | 8 | 7.5 | 8 | 0 | 0.0 |
| M/23 | 10 | 5.5 | 3 | 4.5 | 3 | -1 | -1.2 |
| F/50 | 85 | 6.5 | 6 | 7 | 6 | 0.5 | 0.1 |
| F/41 | 60 | 6.5 | 6 | 9 | 9 | 2.5 | 0.5 |
| F/35 | 126 | 8 | 8 | 8 | 9 | 0 | 0.0 |
| MEDIAN | 60 | 7.0 | 7.0 | 8.0 | 8.0 | 0.5 | 0.09 |

EXACERBATING PROGRESSIVE MS

| SEX/AGE | Mos. On PICLC | EDSS-E | AI-E | EDSS-L | AI-L | EDSS Change | Change Per yr. |
|---|---|---|---|---|---|---|---|
| F/36 | 4 | 9 | 9 | 3 | 2 | -6 | -18.0 |
| F/34 | 35 | 5.5 | 2 | 6 | 3 | 0.5 | 0.2 |
| F/26 | 68 | 4.5 | 0 | 5 | 2 | 0.5 | 0.1 |
| F/55 | 85 | 4 | 2 | 3.5 | 2 | -0.5 | -0.1 |
| F/35 | 84 | 3 | 2 | 3.5 | 3 | 0.5 | 0.1 |
| M/42 | 28 | 6 | 4 | 6 | 4 | 0 | 0.0 |
| F/25 | 63 | 9.5 | 9 | 4 | 2 | -5.5 | -1.0 |
| M/22 | 3 | 8.5 | 9 | 6 | 6 | -2.5 | -10.0 |
| F/14 | 57 | 8.5 | 9 | 4.5 | 2 | -4 | -0.8 |
| F/34 | 9 | 8.5 | 9 | 8.5 | 8 | 0 | 0.0 |
| F/29 | 12 | 5 | 3 | 1 | 1 | -4 | -4.0 |
| F/34 | 25 | 5.5 | 3 | 5.5 | 3 | 0 | 0.0 |
| F/17 | 83 | 9.5 | 9 | 3 | 2 | -6.5 | -0.9 |
| MEDIAN | 35 | 6.0 | 4.0 | 4.5 | 2.0 | -0.5 | -0.1 |

EDSS-E = Kurtzke Disability Status Score on Entry; EDSS-L = EDSS at Last examination; EDSS range from 1 (mild MS) to 9 (totally disabled)
AI-E = Ambulation Index on study entry; AI-L = AI at Last Examination
AI ranges from 1 (minimal disability) to 9 (bedridden)

METHOD FOR THERAPEUTIC, CLINICAL AND VETERINARY USE POLY-ICLC

This application is a Continuation in Part of U.S. patent application Ser. No. 10/611,614 filed Jul. 1, 2003 and now U.S. Pat. No. 7,439,349, incorporates by reference U.S. Pat. No. 4,349,538 (Hilton B LEVY), U.S. Pat. No. 6,468,558 (Jonathan P Wong), published U.S. Patent application 200610223742 A1 (Andres M Salazar), U.S. patent application Ser. No. 10/611,614 (Andres M. Salazar) and published U.S. Patent application 60/995,313 (Andres M. Salazar).

FIELD AND BACKGROUND OF THE INVENTION

1. Field of the Invention

The present invention relates in general to methods of administration of pharmaceutical compounds, and more particularly to, polyriboinosinic-polyribocytidylic acid stabilized with polylysine and carboxymethylcellulose (Poly-ICLC).

2. Background Information

The invention described and claimed herein comprises an improved method for using Poly-ICLC suitable for clinical use with reduced toxicity at effective dose levels, and a method for using Poly-ICLC clinically to treat various conditions and to regulate genes in humans.

U.S. Pat. No. 4,349,538 (Hilton B LEVY) and application Ser. No. 10/611,614 (Andres M. Salazar) describe the preparation and clinical use of Poly-ICLC. However, the high doses (>300 mcg/kg) described clinically by Levy were intended to induce interferon and proved to be toxic and largely ineffectual for treatment of human patients, to the extent that, after many attempts, the experimental clinical use of poly-ICLC was largely discontinued almost two decades ago. Thus, over 25 years after it was first disclosed, poly-ICLC has yet to be approved by the US Food and Drug Administration for any therapeutic indication.

Polyinosinic-Polycytidylic acid stabilized with polylysine and carboxymethylcellulose (Poly-ICLC) is a synthetic complex of polyinosinic and polycytidylic acid (double-stranded RNA (dsRNA)), stabilized with polylysine and carboxymethyl cellulose that was used as an interferon inducer at high doses (up to 300 mcg/kg IV) in short-term cancer trials some years ago. This gave mixed results with moderate toxicity, and the use of Poly-ICLC was generally abandoned when recombinant interferons became available. However, lower dose (10 to 50 mcg/kg) poly-ICLC results in a broader host defense stimulation, and enhanced clinical activity with little or no toxicity. As such it represents an example of broad spectrum host-targeted therapeutics, in contrast to conventional antibiotics, antiviral or antineoplastic agents that target specific organisms or tumors. (Salazar, Levy et al. 1996) (Ewel, Urba et al. 1992) (Levy and Salazar 1992) (Talmadge and Hartman 1985) (Maluish, Reid et al. 1985).

There are at least four closely interrelated clinical actions of poly-ICLC, any of which (alone or in combination) might be responsible for its antitumor and antiviral activity. These are 1) its induction of interferons cytokines and chemokines; 2) its broad immune enhancing effect; 3) its activation of specific dsRNA dependent enzymes, such as oligoadenylate synthetase (OAS), the p68 protein kinase (PKR), and the RIG-I Helicase, and MDA5; and 4) its multidimensional gene regulatory actions.

Interferon, Cytokine and Chemokine Induction.

Induction of interferons, cytokines and chemokines is one of the important mechanisms for the action of poly-ICLC, particularly in the activation of innate immunity and the antiviral state. While interferon alone does not appear to be sufficient treatment for many conditions it has become increasingly clear that a 'natural mix' of interferons, cytokines, and chemokines, such as those induced by the disclosed clinical regimen of Poly-ICLC, play a critical role not only in establishment of innate immunity, but in major elements of adaptive immunity, such as maturation of dendritic cells and targeting by antigen specific T cells.

Immune Modulation:

Low dose Poly-ICLC thus also has a complex immune enhancing action for which type 1 interferon induction appears to be necessary but is not sufficient. This includes, T-cell and natural killer cell activation, myeloid dendritic cell activation via TLR3, and a potent adjuvant effect with increased antibody response to antigen. (Levy and Bever 1988) For example, administration of low doses of poly-ICLC along with swine flu vaccination in monkeys dramatically accelerates and increases HAI antibody titres. (Stephen, Hilmas et al. 1977) The complex interactions of the dsRNAs and the interferons in this regard are still incompletely understood, yet this seemingly paradoxical dual role of poly-ICLC as an antiviral agent and immune enhancer is consistent with its function in establishing an immediate defense system against viral attack while at the same time facilitating the establishment of long term immunity. Thus, in contrast to conventional antiviral agents, poly-ICLC does not inhibit and could enhance concomitantly administered vaccines, including live virus vaccines such as smallpox vaccine that carry significant morbidity related to uncontrolled vaccine virus proliferation. In contrast to vaccination, the protective effect of dsRNAs such as poly-ICLC is also much more rapid, since the antiviral state is established within hours.

"Catalytic" Action of Poly-ICLC: OAS and PKR

The third action of Poly-ICLC is a more direct antiviral and antineoplastic effect mediated by at least four interferon-inducible nuclear enzyme systems, the 2'5' oligoadenylate synthetase (OAS) and the P1/eIF2a kinase, also known as the dsRNA dependent P68 protein kinase (PKR). (Jacobs and Langland 1996) DsRNA is not a normal component of mammalian cells, but is a byproduct of many viral infections. When presented to the body it thus activates a panoply of host defenses. DsRNA induces an antiviral state in cells by functioning as an obligatory cofactor for OAS, which activates ribonuclease-L, as well as for the PKR, which inhibits initiation of protein synthesis, for the recently described RIG-I Helicase and melanoma-differentiation associated-gene-5 (MDA5) A5 (Yoneyama, Kikuchi et al. 2004), (Kato, Takeuchi et al. 2006), and for an aminotransferase that is less well studied. This may help explain the demonstrated preferential decrease of tumor protein synthesis in vivo by poly-ICLC.

The OAS and PKR are very sensitive to dsRNA dose and structure (Minks, West et al. 1979). For example, simple, long chain dsRNA (as in poly-ICLC) is the most potent stimulator of OAS and PKR, while mismatched or irregular dsRNA can be inhibitory. Similarly, the PKR has both high and low affinity binding sites and is inhibited by too high a dose of dsRNA. (Galabru, Katze et al. 1989) Clinically, the OAS response is also maximal at a dose of about 30 mcg/kg Poly-ICLC, and is much diminished above 100 mcg/kg (M. Kende, N. Bemton, et al., Unpublished).

The inhibition of EFC2 glioma cells in vitro by interferon beta is also significantly associated with activation of both the OAS and PKR. Others have demonstrated that expression of a functionally defective mutant of the PKR results in malignant transformation in vitro, suggesting an important role for this enzyme in suppression of tumorigenesis. (Koromilas, Roy et al. 1992) Both PKR and poly-IC are now know to regulate the p53 tumor suppressor gene, which in turn is associated with the multiple malignancy Li-Fraumeni syndrome, which includes astrocytomas, sarcomas, lung, and breast cancers.

The clinical half-life of the OAS response to IM Poly-ICLC is about 2.5 days, suggesting an optimum dose schedule of two or three times per week (M. Kende, N. Bernton, et al., Unpublished). Patients treated with Poly-ICLC showed up to a 40-fold increase in serum OAS product in response to treatment at 10 to 20 mcg/kg, and a significant association of serum OAS with tumor response (p=0.03). Mediation of anti-tumor action by OAS and/or PKR activation could help explain why the high doses of Poly-ICLC used in early cancer trials were relatively ineffective.

Many viruses, including but not limited to adenovirus, pox viruses (vaccinia), foot and mouth virus, influenza, hepatitis, poliovirus, herpes simplex, SV-40, reovirus, SARS coronavirus, ebola virus, flaviviruses, and the human immunodeficiency virus (HIV) circumvent host defenses by down regulating OAS and/or PKR, and this effect can be reversed in vitro by exogenous dsRNA. (Jacobs and Langland 1996) A block of either PKR and/or OAS-mediated interferon action might also explain the variable response to interferons seen in both microbial and neoplastic disease. Certain viruses as well as neoplasms such as malignant gliomas may use this or a similar mechanism to circumvent host defenses and cause disease. Those diseases may thus be among the prime targets for clinical Poly-ICLC therapy using the method described herein that maximizes PKR activation.

Poly-ICLC has thus been demonstrated to have significant antiviral action against a broad variety of virus families. One example is the inhibition of vaccinia virus in several models (Levy and Lvovsky 1978), (Burgasova 1977) (Baron, Salazar et al. 2003) Levy & Lvovsky used poly-ICLC or placebo topical ointment in rabbits and subsequently inoculated them with intradermal injections of vaccinia virus in 10 adjacent skin sites. Local treatments were repeated at 1, 2, 3, and 4 days. Animals treated with placebo ointment developed severe lesions from days 3 to 6, and three of the eight died with vaccinia encephalitis. In contrast, poly-ICLC treated animals showed no signs of systemic disease and had much smaller skin lesions, rarely progressing beyond 1-3 mm. In separate experiments, poly-ICLC was also effective when applied after the lesions became visible. Viral titers in the skin lesions were markedly decreased (by 3 logs) in the treated animals, and interferon titers were increased. However, the mean virus-neutralizing antibody titers in the serum at 10 days was increased about 10-fold in the treated animals compared to placebo controls. While the authors appeared to suggest that the beneficial effects were due to local skin action of the poly-ICLC, they also demonstrated a robust systemic (serum) interferon response to the topical administration of the drug. This suggests that the principal protective effect may actually be systemic, which is further supported by the marked decrease or possible abrogation of systemic vaccinia dissemination by the topical poly-ICLC in their experiments.

The interaction of the type I interferons and poly-ICLC with each other in protection of the host from viral or neoplastic challenges remains unclear partly because of their overlapping functions. Nevertheless, the relationship of Poly-ICLC and the interferons can be manipulated to therapeutic advantage, At moderate to high doses, poly-ICLC is a powerful inducer of interferons, which in turn can induce synthesis of enzymes systems such as the OAS, PKR, RIG-I, MDA-5, and others that themselves ultimately regulate specific protein synthesis. But, as noted above, the OAS, PKR, and likely others also require low-dose dsRNAs as obligatory cofactors to function, particularly if they have been blocked by viral and or tumor evasive factors. Low dose poly-ICLC is particularly effective clinically in this regard when administered in the regimen described in item 6 under 'Summary of the Invention' below.

Clinical Gene Regulation is a fourth mechanism by which Poly-ICLC can modify the biologic response and provide therapeutic benefit.

Plain, unstabilized poly-IC has been shown to up-regulate or down-regulate a broad variety of over 270 genes in cell culture (Geiss, Jin et al. 2001). However plain poly-IC is not effective in vivo in primates and many other species, and is of limited clinical utility. On the other hand, Poly-ICLC has broad gene regulatory actions when administered clinically in humans. These genes include but are not limited to the RIG-I helicase, interferon induced protein (p56) (please see example), tumor necrosis factor, interferon regulatory factor, matrix metalloproteinase, plasminogen activator, tumor protein p53, fibroblast growth factor, eukaryotic initiation factor 2, actin filament-associated protein, VCAM-1, OAS, PKR, Toll-like receptor 3, type 1 interferons, Tumor necrosis factor (TNF), Interleukin 6, interleukin 10 and other cytokines and chemokines. Some of these genes play critical roles in the body's natural defenses against a variety of neoplasms and microbial infections, and in controlling other cell functions, including protein synthesis, atherogenesis, programmed (apoptotic) cell death, cell metabolism, cellular growth, the cytoskeleton and the extracellular matrix. Gene activation is transient, lasting 24-48 hours, suggesting that repeated dosing at 2-3 day intervals will be necessary to achieve a therapeutic effect in some conditions. This is the schedule of administration that was used successfully in treatment of malignant gliomas and is further described below. (See below). For chronic or long term degenerative conditions administration may need to be extended for a period of years.

Prevention and Treatment of Ionizing Radiation Injury

Another action of dsRNAs and poly-ICLC in particular is its demonstrated protection from radiation injury. (Baze, Lvovsky et al. 1979), (Lvovsky, Levine et al. 1982) In one set of experiments, mice were treated with poly-ICLC intramuscularly at doses of 0.1 to 3 mg/kg before receiving an LD50 (30d) of ionizing radiation. Animals received either single or multiple treatments with PICLC at 8-72 hours prior to radiation exposure. Treated animals had a significantly increased survival, with a maximum dose reduction factor of 1.25. Thirty-day survival was increased by as much as 60% at a dose of about 700 Rads (From 33 to 93%). The time of maximum radioprotection did not coincide with induction of interferon, which occurred 24-48 hours earlier. This suggests that induction of enzymes such as the PKR and OAS may be more important to the radioprotective effect than simple induction of interferon. As noted above, the maximum OAS response after PICLC is about 48-72 hours after treatment with IM Poly-ICLC and coincides with the time of maximum radioprotection. Thus, a dosing schedule that maximizes not only OAS and PKR induction, but also their subsequent activation would promise an even greater radioprotective effect.

Data will be presented demonstrating the radioprotective effect of Poly-ICLC when given according to the double-dosing regimen described below that maximizes OAS and PKR activation.

SUMMARY OF THE INVENTION

The foregoing problems are overcome, and other advantages are provided by, an improved, non-toxic method for utilizing Poly-ICLC in humans clinically intranasally, topically, orally, sublingually, intravenously and/or intramuscularly to modulate the expression of a broad range of genes. Similar effects have been demonstrated for plain, unstabilized poly-IC in cell culture (Geiss, Jin et al. 2001), although plain poly-IC is not effective in primates and many other species. These genes include but are not limited to the helicase, interferon induced protein (p56), tumor necrosis factor, interferon regulatory factor, matrix metalloproteinase, plasminogen activator, tumor protein p53, fibroblast growth factor, eukaryotic initiation factor 2, actin filament-associated protein, and VCAM-1. Some of these genes play critical roles in the body's natural defenses against a variety of neoplasms and microbial infections, and in controlling other cell functions, including protein synthesis, atherogenesis, programmed (apoptotic) cell death, cell metabolism, cellular growth, the cytoskeleton and the extracellular matrix. Poly-ICLC will therefore be of clinical utility in diseases in which expression of one or more of these genes is abnormal. Further, applications include similar regulation of genes in various animal species, including primates, carnivores, ungulates, and poultry.

In accordance with a second aspect of the invention, an improved method of administration (intranasally, orally, sublingually, intramuscularly, intravenously or topically) comprises administration in at least two doses spaced 4-72 hours apart, where the first dose is in a moderate range (30 to 100 mcg/kg in humans) sufficient to induce measurable but not excessive levels of serum interferon and maximal levels of PKR, OAS, RIG-I, TLR3 and other dsRNA dependent host defenses; and the second, lower dose is in the maximally effective range (10 to 40 mcg/kg in humans) for unblocking and stimulation of certain interferon and dsRNA inducible enzyme systems, including the PKR and 2'5'OAS, which reach their serum peaks some 24 to 48 hours post initial Poly-ICLC dosing. This approach may be extended to the use of other stabilized dsRNAs to achieve the same results. The dosing cycle may be repeated at weekly or twice weekly intervals for a varying number of cycles depending on the chronicity of the disease being treated, and may be continued for a prolonged period of time (months to several years). Finally, one or more of the dosages may be delivered utilizing a dermal patch or transdermal vehicle. (See section II under Preferred Embodiments)

Dose cycles may be repeated weekly or twice weekly; dose cycles may be repeated weekly or twice weekly for at least a month; dose cycles may be repeated weekly or twice weekly for at least a year.

In accordance with a third aspect of the invention, Poly-ICLC is administered clinically as above to treat certain neoplastic diseases in humans. These include but are not limited to malignant brain tumors, melanoma, breast and lung cancer, colon cancer, sarcomas, renal cell cancer, and certain leukemias and lymphomas. (See below)

In accordance with a fourth aspect of the invention, an improved, non-toxic method for utilizing Poly-ICLC clinically as above to prevent and treat microbial infections in humans by a number of viruses. These include but are not limited to arboviruses and flaviviruses such as yellow fever, West Nile virus, Japanese encephalitis and dengue, filoviruses such as ebola, influenza, poxviruses such as smallpox and monkeypox, adenovirus, hepatitis, coronaviruses such as the SARS virus, herpesviruses such as herpes simplex and the human immunodeficiency virus (HIV) Certain of these viruses survive in the body by down-regulating some of the systems cited above. Further, applications include similar treatment of various animal species, including primates, carnivores, ungulates, poultry, and other birds, and include (but are not limited to) arboviruses infections such as equine encephalitis, foot & mouth virus, influenza, arteriviruses such as the Porcine PRRS virus, and bovine respiratory complex.

Further applications of the same basic invention include improved, non-toxic method for utilizing Poly-ICLC clinically as above to prevent and treat certain microbial bacterial and parasitic infections, including malaria and leishmaniasis.

Various immune disorders can also be treated with this method, including, but not limited to multiple sclerosis, Guillain Barre syndrome, immune neuropathies, and certain dysimmune vasculitides; and ionizing radiation injury.

In accordance with a fifth aspect of the invention, an improved, non-toxic method for utilizing Poly-ICLC clinically in humans as above to enhance the action and decrease the toxicity of various vaccines, including live virus vaccines.

It is therefore an object of the invention to provide an improved method for administration of Poly-ICLC that results in markedly decreased toxicity, and marked enhancement of its clinical and veterinary uses and its multidimensional biological effects.

BRIEF DESCRIPTION OF THE DRAWINGS

FIG. 1 is an unpublished table demonstrating marked clinical induction in humans of the antiproliferative and immune regulatory gene product P56. WBC of glioma patients receiving the regimen of poly-ICLC herein described IM showed enhanced expression of P56 on RT-PCR by 40 to 400 fold at 24 hours after the first dose. (Sen, Salazar, et al)

FIG. 2 is a table demonstrating markedly increased survival of malignant glioma patients treated with 20 mcg/kg poly-ICLC IM, plus chemotherapy, using the repeated dosing regimen described two to three times weekly for up to 4 years. This effect is mediated by activation of various elements of innate immunity by the poly-ICLC. This protection may involve both antiproliferative mechanisms involving reactivation of OAS and PKR, as discussed above, as well as induction and maintenance of an adaptive immune response to tumor cells. Induction of an immune response to tumor antigens released by chemotherapy is facilitated by TLR3 and other dsRNA signaling on immune cells, while maintenance and targeting may also be facilitated by TLR3 receptors on cerebral glia and tumor cells as well as vascular endothelial cells. (Updated from Salazar, et al, 1996)

FIG. 3 Protection from Lethal SARS Challenge by Nasal Poly-ICLC

Mice were treated with the indicated regimen of nasal poly-ICLC prior to or after challenge with a lethal dose of SARS Coronavirus. Primary outcome was survival, as indicated. (Barnard D, Salazar A M, et al, unpublished)

FIG. 4 is an unpublished table showing decrease or stabilization of HIV viral load in blood after treatment of advanced AIDS patients with low dose, long term poly-ICLC. Additional data in the same patients shows stabilization or improvement of T4 cell counts, indicating at least partial reversal of viral induced immunosuppression. (Please see Example A, page 30 [NOT SURE WHAT THIS REFERS TO])

FIG. 5 is an unpublished table showing low dose, long term IM poly-ICLC treatment of patients with Progressive Multiple Sclerosis, showing relative stabilization and or improvement of neurological status. This is possibly mediated by poly-ICLC modulation of interferon, major histocompatibility complex (MHC) expression, and/or T regulatory cells. (Please see Example E, page 31 [WHAT DOES THIS REFER TO?].)

DESCRIPTION OF THE PREFERRED EMBODIMENTS

The invention is a novel method for clinical use of Poly-ICLC with reduced toxicity at effective dose levels, and method for using Poly-ICLC to regulate genes and treat certain disease conditions.

I. Phased Multi-Dose Treatment

The complex interaction of the interferons and dsRNA-activated systems can be manipulated to therapeutic advantage, particularly in the case of those certain microbial and neoplastic diseases that thrive by circumventing host defense mechanisms such as those involving the OAS, PKR, RIG-I, MDA5, and TLR.

One approach described by Marcus and colleagues in avian cell culture uses the combination of exogenous interferon followed by dsRNA in that order to achieve an up to 100-fold increased level of protection against avian reovirus and Newcastle disease virus over that provided by either agent alone or when given in the reverse order (Marcus and Sekellick 2001). A similar rationale can be used to treat certain human and veterinary infectious and neoplastic diseases utilizing Poly-ICLC alone. In this context, Poly-ICLC is serving two functions; first the induction of interferon and gene expression for OAS, PKR, RIG-I TLR3 and certain other proteins, and second the activation of these previously induced dsRNA dependent systems such as OAS, PKR, and other enzymes. This approach better mimics the repeated dsRNA presentation to the host that results from most viral replication, but that is missing or is inhibited by evasive mechanisms in most cancers, viral infections, or with most vaccines.

The approach described here is to first stimulate interferon induction with a moderate to high dose of Poly-ICLC, allow 4-72 hours for interferon induction of OAS, PKR and other genes, and then activate them with a second, lower dose of Poly-ICLC. Given the short (2-3 day) half-life of these systems, this cycle may need to be repeated at least once or twice a week for a variable period of time depending on the disease in question. In some infections, such as mouse influenza, a single two-dose cycle of intranasal Poly-ICLC (1 mg/kg) has been shown to protect from lethal viral challenge for as long as two weeks, although the authors did not specifically pursue the high dose-low dose sequence disclosed here (Wong, Saravolac et al. 1995) A single dose cycle was less effective.

Likewise, in the treatment of malignant gliomas, we found that less than twice weekly Poly-ICLC dosing appeared ineffectual. (Salazar, Levy et al. 1996) In that successful clinical trial (further described in the example below), dosing was spaced at 48 hours. Thus the second dose of Poly-ICLC was given at a time when the OAS (and presumably PKR) had reached peak blood levels from the first dose and could be most effectively activated by the Poly-ICLC.

Clinical trials of poly-ICLC to date have utilized the intravenous (IV) or intramuscular (IM) routes of administration. We have demonstrated that intranasal Poly-ICLC can protect from otherwise lethal nasal SARS coronavirus challenge in mice (Barnard, Salazar, et al, unpublished, See FIG. 3. We have now have demonstrated that intranasal treatment of non-human primates (rhesus monkeys) with Poly-ICLC will also result in a robust systemic response as measured by plasma interferon at 24 hours, but not 8 hours from administration, and as shown in FIG. 1. This unexpected result opens the possibility of using intranasal, sublingual, or topical Poly-ICLC for treatment of systemic diseases. This may be especially advantageous in long term treatment of cancer or autoimmune diseases, treatment of large number of individuals exposed to a bioterror threat such as smallpox; or for veterinary use, as in containment of an outbreak of foot and mouth disease in cattle, management of the bovine respiratory complex, avian influenza, or the porcine reproductive-respiratory syndrome (PRRS)

Similarly, it is also expected that orally or sublingually administered Poly-ICLC may be sufficient to yield a clinical therapeutic response. Oral administration could also be especially advantageous in large-scale human or veterinary uses. Finally, older rabbit studies demonstrated protection from vaccinia by topically administered Poly-ICLC. This suggests that topical administration of Poly-ICLC in a dermatologic preparation or dermal patch may also be efficacious for certain applications in humans (Levy and Lvovsky 1978). Further data will be presented to address these claims.

EXAMPLES

An Improved Method for the Clinical and Veterinary Use of Poly-ICLC

Poly-ICLC, especially as improved as described above, has application to the treatment of a variety of diseases including certain neoplastic, infectious, and autoimmune disorders.

The following examples are illustrations, but not limitations, of the approach. Given these examples, one of ordinary skill in the art could apply the same approach to other diseases.

A) Example of Clinical Gene Modulation by Poly-ICLC in Primates, Including Man

Human patients with recurrent malignant gliomas undergoing therapy with poly-ICLC (20 mcg/kg IM 3 times per week) had blood drawn at baseline and 24 hours after the first injection, White cells were isolated and frozen. RTPCR was used to evaluate the expression of the gene for interferon inducible p56 enzyme in WBC. The figure shows up to a several hundred-fold increase in gene expression at 24 hours. (Sen G, Salazar A M, et al, unpublished) (See FIG. 1)

Additional studies will further demonstrate the spectrum of gene activation, including but not limited to the following genes: helicase, and, tumor necrosis factor, interferon regulatory factor, matrix metalloproteinase, plasminogen activator, tumor protein p53, fibroblast growth factor, eukaryotic initiation factor 2, actin filament-associated protein, and VCAM-1. These studies will not only demonstrate the spectrum of gene activation in humans by low dose Poly-ICLC, but will also reveal possible correlations to tumor response. Nevertheless, the potential clinical therapeutic uses of the ability to regulate such a broad variety of genes extends beyond the infection and neoplasm treatments described below.

B) Example of Clinical Cancer Treatment: Treatment of Malignant Gliomas

Poly-ICLC (10 to 50 mcg/kg intramuscularly one to three times weekly) was given for up to 56 months to 38 patients with glioblastoma multiforme or anaplastic astrocytoma. (Salazar, Levy et al. 1996) There was relatively low or no toxicity. Twenty of 30 patients (66%) receiving at least twice weekly Poly-ICLC (including all anaplastic astrocytoma patients) showed regression or stabilization of enhancing tumor on MRI (median=65% volume decrease). Only two of the 11 anaplastic astrocytoma patients subsequently showed tumor recurrence while on Poly-ICLC, and most of the group remain alive, with a median progression-free follow-up of over 65 years from diagnosis (range 22-134+ months). Median overall survival is now 111+ months (range 34-134+). Median Kaplan-Meir survival for glioblastoma patients on at least twice weekly Poly-ICLC treatments was 19 months; only one remains alive (98 months from diagnosis). Tumor response was associated with 2'5' oligoadenylate synthetase activation (p=0.03), but not with serum interferon, interleukins, or neopterin.

The 100% sustained tumor response or stable rate, and the prolonged, continuing, quality survival in anaplastic astrocytoma patients on Poly-ICLC contrasts favorably with the expected median survival of about 26 months for newly diagnosed AA patients on traditional chemotherapy. As suggested above, it is expected that even better survivals than those seen to date may be achievable utilizing a new double-dosing technique, as follows:

Poly-ICLC is administered intranasally, orally, sublingually, intramuscularly, intravenously or topically in at least two doses spaced 4-72 hours apart. Preferably, the first dose is in a moderate range sufficient to induce measurable but not excessive levels of serum interferon (30 to 100 mcg/kg in humans); and the second, lower dose is in the maximally effective range for unblocking and stimulation of certain interferon and dsRNA inducible enzyme systems, including the PKR and 2'5'OAS, which reach their serum peaks some 48 hours post initial Poly-ICLC dosing. For humans, the first dose would preferably be in the range of 30 to 100 mcg/kg and the second dose would preferably be in the range of 10 to 40 mcg/kg. Preferably, the doses would be spaced approximately 48 hours apart.

(See updated, unpublished survival data in table in FIG. 2)

It is expected that this could be confirmed or suitably modified by those skilled in the art, based on the outcome of ongoing phase II clinical trials of Poly-ICLC for patients with malignant brain tumors.

A number of cancers share various characteristics with malignant gliomas, and likely utilize similar mechanisms to avoid host defenses. Such cancers may thus also be amenable to Poly-ICLC treatment using the regimen described herein. They include melanoma, and certain leukemias and lymphomas, which share abnormalities on chromosome 9p; renal cell carcinoma; and sarcomas, lung, breast, and colon cancers that occur together with gliomas in the familial Li-Fraumeni syndrome.

C. Example of Use of Nasal Poly-ICLC for Prevention of SARS CoV Infection.

SARS ('severe acute respiratory syndrome), is a classical example of the danger posed by emerging pathogens. It appeared in Asia in 2003 and rapidly became a global outbreak, even before the causative agent, a rare coronavirus, was identified. There was no effective treatment and of 8,000 cases worldwide, nearly 800 died. Beyond the human loss, the economic disruption was considerable.

We have now demonstrated complete protection by nasally administered [POLY-ICLC] in an otherwise lethal murine challenge models of SARS. [POLY-ICLC] appears to be the most effective such treatment tested to date and has become the 'treatment control' or 'gold standard' of therapy in this model.

Mice were treated with 0.25 to 1 mcg/kg of nasal poly-ICLC prior to or after challenge with a lethal dose of SARS Coronavirus. Primary outcome was survival, as indicated. Pretreatment with even 0.25 mg/kg poly-ICLC in repeated doses at 24 hour intervals provided total protection from an otherwise lethal viral challenge. (Barnard D, Salazar A M, et al, unpublished) See FIG. 3.

These studies are further evidence of the potential utility of nasal poly-ICLC for providing immediate broad spectrum protection and epidemic containment in the case of an intentional (bioterror) or unintentional outbreak of infections with emerging respiratory pathogens.

D) Example of Clinical Treatment of a Retroviral Disease:

Treatment of AIDS with Poly-ICLC. In an open pilot trial, low dose (0.2-2 mg) PICLC was administered intramuscularly (IM) 1-3 times per week with or without Zidovudine over up to 30 months to 22 patients with HIV infection or AIDS. (Salazar, Morales et al. 1990) PICLC was well tolerated, with no significant clinical or laboratory toxicity. Side effects consisted of a mild 12-24 hour flu-like syndrome with low-grade fever and malaise at the higher doses, but usually disappeared after the first half-dozen treatments. 12/20 patients showed at times dramatic initial rises in T-4 cell counts along with symptomatic improvement, although this was not uniformly maintained. Plasma P-24 titers (a measure of viral load), which were positive in 8/16 patients before biweekly treatment, either became undetectable or remained so in all but one patient, whose titers were markedly elevated at onset and dropped by 75% with treatment.

In a separate dosing study of PICLC in 8 AIDS patients, neuropyschological testing has shown a marked improvement in choice reaction time and the Purdue pegboard test at 16 weeks of treatment, with a deterioration back to baseline when PICLC was discontinued. (Salazar, Martin, unpublished). This contrasts with a gradual, statistically significant deterioration in choice reaction time seen in an untreated HIV+cohort (N=41) over six months. As suggested above, it is expected that even better responses than those seen to date may be achievable utilizing the new double-dosing technique described in Section B, above, and shown in FIG. 4.

E) Example of Poly-ICLC Treatment of an Autoimmune Disorder: Treatment of Multiple Sclerosis An open trial of high dose (100 mcg/kg) intravenous PICLC showed moderate acute toxicity in 15 patients with chronic MS; several patients improved or stabilized, but deteriorated when drug was stopped, as reported by Bever, Salazar, et al., 1986. (Bever, Salazar et al. 1986) Subsequently, Salazar continued to treat some of these and other MS patients with a completely new extended regimen using much lower doses of PICLC intramuscularly over a longer period of time. Results of this follow-up study are unpublished, and are disclosed below and in FIG. 5

Methods: Thirty one patients with either chronic progressive (CP) or exacerbating progressive (EP) multiple sclerosis received 5-100 mcgm/kg PICLC IM q 3-14 days for up to 15 years; most received a median dose of 10 mcg/kg weekly.

Toxicity was markedly reduced to an inconstant, mild, transient malaise. The Kurtzke Expanded Disability Status Score (EDSS, which varies between 0 (normal) and 9 (totally bedridden and dependent) was used to evaluate outcome. As shown in FIG. 6, the EDSS remained stable or improved in 15/31 patients (dramatically in 5). Six patients deteriorated when PICLC was stopped. The 19 CP patients showed a median EDSS change of 0.09 points per year over a median of 60 months; while the 12 EP patients showed a slight improvement (−0.1 EDSS per year) over a median of 28 months. These rates compare very favorably with the expected rates of progression in untreated multiple sclerosis patients. (Note that a lower Kurtzke score is better).

Therefore, IM low dose PICLC may be a valuable alternative to the more expensive and toxic beta-interferons for long-term management of MS. As suggested above, it is expected that even better response rates than those seen to date may be achievable utilizing the new double-dosing technique described above.

IV. A Clinical Method for Increasing the Speed and Efficacy and Decreasing the Toxicity of Vaccines.).

The strategy presented here is designed to simultaneously control vaccine side effects by decreasing viral proliferation while at the same time targeting the relevant antigens for an immune response to vaccination. It does so by stimulating the host's natural immediate response mechanisms to viral infection, including local dendritic cell activation at the time of vaccination through IM or topical administration of Poly-ICLC at the time of vaccination.

While illustrated with respect to a to method for producing large lots of final sterile Poly-ICLC suitable for clinical use with reduced toxicity at effective dose levels, and method for using Poly-ICLC to regulate genes, and manage certain disease conditions, the invention may be applied to any method for producing large lots of final sterile Poly-ICLC suitable for clinical use with reduced toxicity at effective dose levels, and method for using Poly-ICLC to regulate genes using the same techniques, modified to adapt to method for producing large lots of final sterile Poly-ICLC suitable for clinical use with reduced toxicity at effective dose levels, and method for using Poly-ICLC to regulate certain genes in a manner which would be known to one skilled in the art.

REFERENCES

Baron, S., A. Salazar, et al. (2003). *Smallpox model: Protection by IFN and Poly-ICLC despite evasive mechanisms*. International Conference on Antiviral Research, Savannah, Ga.

Baze, W., E. Lvovsky, et al. (1979). "Evaluation of a nuclease resistant derivative of polyI polyC (Poly-ICLC) as a radioprotective agent." *Radiation Research* 77: 276-284.

Bever, C., A. Salazar, et al. (1986). "Preliminary trial of poly-ICLC in chronic progressive multiple sclerosis." *Neurology* 36(4): 489-493.

Burgasova, M. (1977). "Study of the antiviral activity of a poly I: Poly-C complex with poly-l-lysine in monkeys." *Antibiotiki* 22(5): 458-60.

Ewel, C., W. Urba, et al. (1992). "Polyinosinic-Polycytidylic acid complexed with poly-L lysine and carboxymethylcellulose in combination with interleukin 2 in patients with cancer: clinical and immunological effects." *Cancer Research* 52: 3005-3010.

Galabru, J., M. Katze, et al. (1989). "The binding of dsRNA and adenovirus VA1 RNA to the interferon-induced protein kinase." *European Journal of Biochemistry* 178; 581-89.

Geiss, G., G. Jin, et al. (2001). "A comprehensive view of regulation of gene expression by double-stranded RNA-mediated cell signaling." *J Biol Chem* 276(32): 30178-30182.

Jacobs, B. and J. Langland (1996). "When two strands are better than one: the mediators and modulators of the cellular responses to double stranded RNA." *Virology* 219: 339-349.

Kato, H., O. Takeuchi, et al. (2006). "Differential roles of MDA5 and RIG-I helicases in the recognition of RNA viruses." *Nature* 441: 101-105.

Koromilas, A., S. Roy, et al. (1992). "Malignant transformation by a mutant of the IFN-inducible dsRNA dependent protein kinase." *Science* 257: 1685-1689.

Levy, H. and C. Bever (1988). Immune modulating effects of PICLC in mice, monkeys, and man. *Applied Bioactive Polymers*. C. Carraher and V. Foster. New York, Plenum.

Levy, H. and E. Lvovsky (1978). "Topical treatment of vaccinia virus infection with an interferon inducer in rabbits." *J Infect Dis* 137(1): 78-81.

Levy, H. and A. Salazar (1992). Interferon inducers. *Interferon: Principles and Medical Applications*. S. Baron, D. Copenhaver, F. Dianzaniet al. Galveston, U. Texas Medical Branch, Galveston: 65-76.

Lvovsky, E., P. Levine, et al. (1982). "Stimulation of hematopoietic stem cells by interferon inducer in non-human primates receiving fractionated total body irradiation." *Int J Radiat Oncol Biol Phys* 8(10): 1721-1726.

Maluish, A., J. Reid, et al. (1985). "Immunomodulatory effect of Poly-ICLC in cancer patients." *J Biol Resp Modif* 4: 656-663.

Minks, M., D. West, et al. (1979). "Structural requirements of dsRNA for the activation of 2'5' oligoA polymerase and protein kinase of interferon treated HeLa cells." *J Biol Chem* 254(20): 10180-10183.

Salazar, A., H. Levy, et al. (1996). "Long-term IM Poly-ICLC treatment of malignant glioma: an open pilot study." *Neurosurgery* 38(6): 1096-1104.

Salazar, A., J. Morales, et al. (1990). "Intramuscular Poly-ICLC in HIV Infection: Preliminary findings." *Neurology* 40(Suppl 1): 238.

Stephen, E., D. Hilmas, et al. (1977). "Swine influenza virus vaccine: potentiation of antibody responses in rhesus monkeys." *Science* 197: 1289-1290.

Talmadge, J. and D. Hartman (1985). "Optimization of an immunotherapeutic protocol with Poly-ICLC." *Journal of Biological Response Modifiers* 4: 484-489.

Wong, J., E. Saravolac, et al. (1995). "Prophylactic and therapeutic efficacies of poly(ICLC) against respiratory influenza A virus infection in mice." *Antimicrob Agents Chemother* 39(11): 2574-2576.

Yoneyama, M., M. Kikuchi, et al. (2004). "The RNA helicase RIG-I has an essential function in dsRNA induced innate antiviral responses." *Nature Immunology* 5(7): 730-737.

What is claimed is:

1. A method for treatment in humans of gliomas, melanoma, breast and lung cancer, colon cancer, sarcomas, renal cell cancer, leukemias, lymphomas, viral infections caused by influenza virus, flavivirus, West Nile virus, Japanese encephalitis virus, dengue virus, yellow fever virus, SARS coronavirus, ebola virus, adenovirus, hepatitis virus, herpesviruses, and human immunodeficiency virus; the autoimmune conditions multiple sclerosis, Guillain Barre syndrome, immune neuropathy, and vasculitis, and ionizing radiation injury; comprising: preparing a Poly-ICLC complex of high molecular weight polyriboinosinic-polyribocytidylic acid double stranded RNA (Poly-IC), low molecular weight poly-l-lysine, and carboxymethylcellulose, by adding poly-L-lysine solution slowly to a carboxymethylcellulose solution over a period of at least 4 days and mixing for the entire blending time vigorously enough to form a vortex and minimize precipitate buildup, followed by addition of the poly-IC component solution; and administering the Poly-ICLC solution intranasally, orally, sublingually, intramuscularly, intravenously, transdermally or topically in at least two doses spaced 4-72 hours apart, where dose is in a range of 10-40 mg/kg body weight in humans sufficient for unblocking and stimulation of interferon and of the dsRNA dependent host defense systems PKR 2'5'OAS, RIG-I Helicase, and Toll-like receptor 3.

2. The method of claim 1 wherein the doses are repeated weekly or every two weeks.

3. The method of claim 1 wherein the dose cycles are repeated weekly or every two weeks for one month to one year.

4. The method of claim 1 wherein the dose cycles are repeated weekly or every two weeks for over one year.

* * * * *